(12) United States Patent
Kim et al.

(10) Patent No.: US 12,283,049 B2
(45) Date of Patent: Apr. 22, 2025

(54) MEDICAL IMAGING APPARATUS FOR OBTAINING MEDICAL IMAGE OF EQUINE AND OPERATING METHOD THEREOF

(71) Applicant: JPIHealthcare. CO., LTD., Seoul (KR)

(72) Inventors: Kyong Woo Kim, Jeonju-si (KR); Hyung Kyu Kim, Siheung-si (KR); Jin Guk Kim, Seoul (KR)

(73) Assignee: JPIHealthcare. CO., LTD., Seoul (KR)

( * ) Notice: Subject to any disclaimer, the term of this patent is extended or adjusted under 35 U.S.C. 154(b) by 422 days.

(21) Appl. No.: 17/968,139

(22) Filed: Oct. 18, 2022

(65) Prior Publication Data
US 2023/0281817 A1   Sep. 7, 2023

(30) Foreign Application Priority Data

Mar. 4, 2022   (KR) .................. 10-2022-0028076

(51) Int. Cl.
*G06K 9/00*   (2022.01)
*G06T 7/00*   (2017.01)
*G16H 30/40*   (2018.01)

(52) U.S. Cl.
CPC ........... *G06T 7/0014* (2013.01); *G16H 30/40* (2018.01); *G06T 2207/10081* (2013.01)

(58) Field of Classification Search
CPC ........ G06T 7/0014; G06T 2207/10081; G16H 30/40; G16H 30/20; G16H 50/20; G16H 50/30; G16H 50/70; A61B 6/10; A61B 6/462; A61B 6/465; A61B 6/469; A61B 6/545; A61B 6/508
See application file for complete search history.

(56) References Cited

FOREIGN PATENT DOCUMENTS

| CN | 105163684 A | * 12/2015 | ......... A61B 17/3421 |
|---|---|---|---|
| CN | 108882899 A | * 11/2018 | ............. A61B 6/032 |
| CN | 109069083 A | * 12/2018 | ............. A61B 34/25 |
| CN | 113870968 A | * 12/2021 | |
| JP | 2007050075 A | 3/2007 | |
| JP | 2017143872 A | 8/2017 | |
| KR | 1020200007298 A | 1/2020 | |
| KR | 102336170 B1 | 12/2021 | |

OTHER PUBLICATIONS

Office Action of KR 10-2022-0028076 dated May 2, 2022.

* cited by examiner

*Primary Examiner* — Xin Jia
(74) *Attorney, Agent, or Firm* — Dinsmore & Shohl LLP; Yongsok Choi, Esq.

(57) ABSTRACT

An operation method of a medical imaging apparatus for capturing an X-ray medical image is provided. The method includes receiving identification information of a user, receiving photographing mode selection information, determining that a photographing mode is an X-ray photographing mode for checking a health condition of an object on the basis of at least one of the identification information of the user and the photographing mode selection information, obtaining identification information of the object, determining an initial photographing position from among a plurality of predetermined photographing positions, and determining a photographing sequence of the plurality of predetermined photographing positions on the basis of the initial photographing position.

7 Claims, 10 Drawing Sheets

FIG. 4

| SEQUENCE NUMBER | PHOTOGRAPHING POSITION |
|---|---|
| 1 | Fore Fetlock Right LM (Lateral/Medical) |
| 2 | Fore Carpus Right DLPMO (Dorsolateeral/palmaromedial) |
| 3 | Fore Carpus Right DMPLO(Dorsomedial/palmarolateral oblique) |
| 4 | Fore Fetlock Right DP (Dorsopalmar) |
| 5 | Hind Fetlock Right LM (Lateral/medial) |
| 6 | Tarsus Right DMPLO |
| 7 | Tarsus Right DLPMO |
| 8 | Hind Fetlock Right DP |
| 9 | Stifle Right OBL (Oblique) |
| 10 | Stifle Right CaCr (Caudocranial) |
| 11 | Fore Fetlock Left LM |
| 12 | Fore Carpus Left DLPMO |
| 13 | Fore Carpus Left DMPLO (PLDMO) |
| 14 | Fore Fetlock Left DP |
| 15 | Hind Fetlock Left LM |
| 16 | Tarsus Left DMPLO (PLDMO) |
| 17 | Tarsus Left DLPMO |
| 18 | Hind Fetlock Left DP |
| 19 | Stifle Left OBL |
| 20 | Stifle Left Cdcr |

400

MEDICAL IMAGING APPARATUS FOR OBTAINING MEDICAL IMAGE OF EQUINE AND OPERATING METHOD THEREOF

CROSS-REFERENCE TO RELATED APPLICATION

This application claims priority to and the benefit of Korean Patent Application No. 2022-0028076, filed on Mar. 4, 2022, the disclosure of which is incorporated herein by reference in its entirety.

BACKGROUND

1. Field of the Invention

The present invention relates to a medical imaging apparatus for obtaining a medical image of an equine and an operating method thereof. More specifically, the medical imaging apparatus provides an optimal path for obtaining a medical image of an equine.

2. Discussion of Related Art

In the case of high-priced equine (racing equine) markets domestically and abroad, in order to check a health condition of an equine, a plurality of medical images, e.g., about 18 to 22 images, are captured and the health condition of the equine is determined based on the plurality of captured medical images. In this case, in order to rapidly capture the plurality of medical images, an X-ray medical imaging apparatus is used. The X-ray medical imaging apparatus is a medical imaging apparatus that transmits X-rays through the human body to obtain an image of an internal structure of the human body. The medical imaging apparatus has advantages in that it is convenient and can obtain a medical image of an object in a short time as compared to other medical imaging apparatuses including a magnetic resonance imaging (MRI) apparatus, a computed tomography (CT) scanning apparatus, and the like.

Before a medical image of an equine is captured, a sedative is injected into the equine to stabilize the equine. However, it is not easy to capture 18 to 22 medical images while stabilizing the equine, and thus there is often a delay, and when there is a delay, the sedative becomes less effective. As the effect of the sedative decreases, the equine may move significantly, and the movement of the equine may threaten the safety of a photographer (user). In fact, many accidents have occurred while medical images of equines are captured.

Therefore, there is a need for a medical imaging apparatus to provide an accurate guide for capturing a medical image of an equine to allow a user to accurately capture the medical image of the equine in a short time.

RELATED ART DOCUMENTS

Patent Document (Patent Document 1) (Korean Patent Registration No. 10-2336170, published on Dec. 8, 2021)

SUMMARY OF THE INVENTION

The present disclosure is directed to providing a medical imaging apparatus, which provides a guide for capturing a plurality of medical images of a single object.

According to an aspect of the present disclosure, there is provided an operation method of a medical imaging apparatus for capturing an X-ray medical image, which includes receiving identification information of a user, receiving photographing mode selection information, determining that a photographing mode is an X-ray photographing mode for checking a health condition of an object on the basis of at least one of the identification information of the user and the photographing mode selection information, obtaining identification information of the object, determining an initial photographing position from among a plurality of predetermined photographing positions, and determining a photographing sequence of the plurality of predetermined photographing positions on the basis of the initial photographing position.

The operating method of the medical imaging apparatus of the present disclosure may further include displaying a plurality of template images for the plurality of predetermined photographing positions according to the photographing sequence, highlighting a template image corresponding to a current photographing position on the basis of the photographing sequence, obtaining a medical image on the basis of the user's input, replacing the template image corresponding to the photographing position of the medical image with the medical image, and highlighting a template image corresponding to a next photographing position after the current photographing position on the basis of the photographing sequence.

In the operating method of the medical imaging apparatus of the present disclosure, one template image among the plurality of template images may include information on a part of the object, information on a position of a detector with respect to the part of the object, and information on a position of a source.

In the operating method of the medical imaging apparatus of the present disclosure, the replacing of the template image with the medical image may include converting the medical image into a black-and-white image, determining whether a pre-stored pattern image appears in the black-and-white image, and when it is determined that the pre-stored pattern image appears in the black-and-white image, replacing the template image corresponding to the photographing position of the medical image with the medical image, wherein the pre-stored pattern image corresponds to the photographing position of the medical image.

The operating method of the medical imaging apparatus of the present disclosure may further include obtaining diagnostic information on the medical image from the user, obtaining a problem area and problem content which are included in the diagnostic information, obtaining a deduction score on the basis of the problem area and the problem content, and outputting the deduction score.

In the operating method of the medical imaging apparatus of the present disclosure, the obtaining of the deduction score may include, when identical diagnostic information is obtained from different medical images obtained by photographing one part of the object at different angles, obtaining the deduction score using only the diagnostic information on one of the different medical images.

In the operating method of the medical imaging apparatus of the present disclosure, the determining of the photographing sequence may include obtaining information on a state of the object in previous photographing on the basis of the identification information of the object, when information on whether an accident occurs, which is included in the information on the state of the object in the previous photographing, indicates that no accident has occurred, obtaining a photographing sequence of the previous photographing, which is included in the information on the state of the object in the previous photographing, and determining that the photographing sequence of the previous photographing is the photographing sequence, wherein the information on the state of the object includes at least one of whether a stabilizer is administered, whether food is ingested before photographing, a photographing sequence, and whether an accident occurs.

In the operating method of the medical imaging apparatus of the present disclosure, the determining of the initial photographing position may include displaying the plurality of template images for the plurality of predetermined photographing positions, obtaining a medical image on the basis of the user's input, determining a similarity between the medical image and each of the plurality of template images, and determining that a photographing position corresponding to a template image having a highest similarity among the plurality of template images is the initial photographing position.

Further, a program for implementing the operating method of the medical imaging apparatus as described above may be recorded on computer readable media.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 4 is a diagram showing a plurality of photographing positions according to an embodiment of the present disclosure;

DETAILED DESCRIPTION

Figure 1:
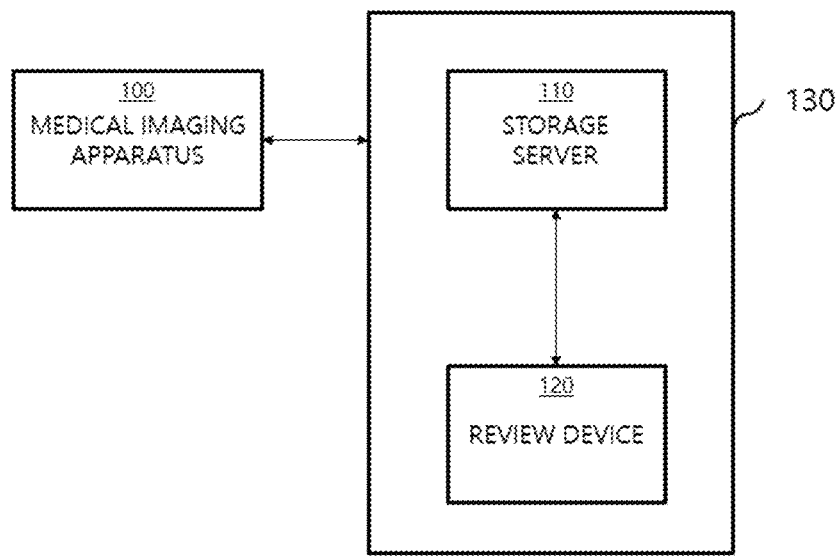
FIG. 1 is a diagram for describing a medical imaging system according to an embodiment of the present disclosure.

Advantages and features of disclosed embodiments and methods of achieving the same will be clearly understood with reference to the accompanying drawings and embodiments described in detail below. However, the present disclosure is not limited to the embodiments to be disclosed below and may be implemented in various different forms. The embodiments are provided in order to fully explain the present embodiments and fully explain the scope of the present invention for those skilled in the art.

Terms used in this specification will be briefly described, and the disclosed embodiments will be described in detail.

Although the terms used herein are selected from among general terms that are currently and widely used in consideration of functions in embodiments of the present invention, these may be changed according to the intentions of those skilled in the art, precedents, or the advent of new technology. In addition, in a specific case, some terms may be arbitrarily selected by applicants. In this case, meanings thereof will be described in detail in a corresponding description of embodiments of the present invention. Therefore, the terms used herein should be defined based on the meanings of the terms and content of this entire specification, rather than simply the terms themselves.

As used herein, the singular forms "a" and "an" are intended to also include the plural forms, unless the context clearly indicates otherwise. Further, the plural forms are intended to also include the singular forms, unless the context clearly indicates otherwise.

Throughout this specification, when a part "includes" an element, another element may be further included, rather than excluding the presence of the other element, unless otherwise described.

Further, the term described in the specification such as "unit" refers to software or a hardware component such as a field-programmable gate array (FPGA) or an application-specific integrated circuit (ASIC), and the unit performs certain functions. However, the "unit" is not limited to software or hardware. The "unit" may reside in an addressable storage medium or may be configured to regenerate at least one processor. Therefore, examples of the "unit" include components such as software components, object-oriented software components, class components and task components, and processes, functions, attributes, procedures, subroutines, segments of program code, drivers, firmware, micro code, circuits, data, databases, data structures, tables, arrays, and variables. Components and functions provided in "units" may be combined into a smaller number of components and "units" or may be further separated into additional components and "units."

According to an embodiment of the present disclosure, the "unit" may be implemented with a processor or a memory. The term "processor" should be interpreted broadly to include a general purpose processor, a central processing unit (CPU), a microprocessor, a digital signal processor (DSP), a controller, a microcontroller, a state machine, or the like. In some environments, the "processor" may refer to an ASIC, a programmable logic device (PLD), a FPGA, or the like. The term "processor" may refer to, for example, combinations of processing devices, such as a combination of a DSP and a microprocessor, a combination of a plurality of microprocessors, a combination of one or more microprocessors in combination with a DSP core, and a combination of any other such components.

The term "memory" should be interpreted broadly to include any electronic component that can store electronic information. The term "memory" may refer to one of various types of processor-readable media, such as a random-access memory (RAM), a read-only memory (ROM), a non-volatile random-access memory (NVRAM), a programmable read-only memory (PROM), an erase-programmable read-only memory (EPROM), an electrically erasable PROM (EEPROM), a flash memory, a magnetic or optical data storage, a register, and the like. When a processor is capable of reading information from and/or writing information to a memory, the memory is said to be in electronic communication with the processor. A memory integrated in a processor is in electronic communication with the processor.

As used herein, the term "image" may refer to multi-dimensional data composed of discrete image elements (e.g., pixels in a two-dimensional (2D) image and voxels in a three-dimensional (3D) image). Examples of the image may include a medical image of an object and the like obtained by a medical imaging apparatus, a CT apparatus, an MRI apparatus, an ultrasound apparatus, other medical imaging apparatuses, etc.

Further, as used herein, the term "object" may be a human, an animal, or a part of a human or animal. For example, the object may include a human, a dog, a cat, an equine, or the like. Further, the object may include at least one of organs, such as a liver, heart, uterus, brain, breast, abdomen, and the like, and blood vessels. Further, the term "object" may be a phantom. The phantom is a material that is very close to the density and effective atomic number of an organism and is very close to the volume of an organism, and may include a spherical phantom having properties similar to a body.

Further, as used herein, the term "user" may be a medical professional, such as a doctor, a nurse, a clinical pathologist, a medical imaging specialist, or the like, and may be a technician repairing a medical device, but the present invention is not limited thereto.

Hereinafter, embodiments will be described in detail with reference to the accompanying drawings so that those of ordinary skill in the art to which the present invention pertains can easily implement them. In addition, in order to clearly describe the present disclosure in the drawings, parts irrelevant to the description will be omitted.

Figure 2:
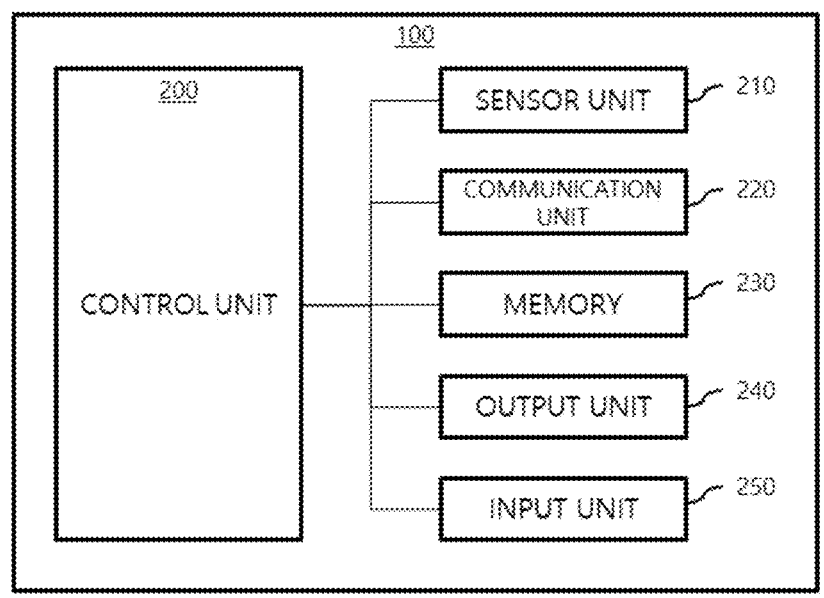
FIG. 2 is a diagram for describing a medical imaging apparatus according to an embodiment of the present disclosure.

FIG. 1 is a diagram for describing a medical imaging system according to an embodiment of the present disclosure. FIG. 2 is a diagram for describing a medical imaging apparatus according to an embodiment of the present disclosure.

Referring to FIG. 1, the medical imaging system may include a medical imaging apparatus 100, a storage server 110, and a review device 120. The medical imaging system may include a workstation 130. The workstation 130 may include the storage server 110 and the review device 120. The storage server 110 and the review device 120 may be implemented in one device, but the present disclosure is not limited thereto, and the storage server 110 and the review device 120 may be implemented in different devices. The medical imaging apparatus 100, the storage server 110, and the review device 120 may transmit or receive data to or from each other using wired/wireless communication.

The medical imaging apparatus 100 may be a stationary medical imaging apparatus or a mobile medical imaging apparatus. Referring to FIG. 2, the medical imaging apparatus 100 may include an X-ray radiation unit, a high voltage generator, a detector, a sensor unit 210, a communication unit 220, a memory 230, an output unit 240, an input unit 250, and a control unit 200. The control unit 200 may control the overall operation of the medical imaging apparatus 100.

The high voltage generator generates a high voltage for generating X-rays and applies the generated high voltage to an X-ray source included in the X-ray radiation unit.

The X-ray radiation unit may include the X-ray source that generates X-rays after receiving the high voltage generated by the high voltage generator. The X-ray source may include an X-ray tube, and the X-ray tube may be implemented as a dipole vacuum tube having a positive electrode and a negative electrode. Further, the X-ray radiation unit may include a collimator that guides a path of the X-rays radiated from the X-ray source to adjust an area to which the X-rays is radiated.

The detector detects the X-rays that are radiated by the X-ray radiator and transmitted through an object. The detector may be a digital detector. The detector may be implemented using a thin-film transistor (TFT) or may be implemented using a charge-coupled device (CCD). The detector may be included in the medical imaging apparatus 100 or may be a separate device that can be detachably connected to the medical imaging apparatus 100.

The medical imaging apparatus 100 may include the sensor unit 210. The sensor unit 210 may obtain various pieces of information using at least one sensor. The sensor unit 210 may be provided as a sensor that uses a measuring means for pressure, potential, optics, or the like. For example, the sensor unit 210 may include at least one of a distance measuring sensor and an encoder. Further, the sensor may include a pressure sensor, an infrared sensor, a light-emitting diode (LED) sensor, a touch sensor, or the like. However, the present disclosure is not limited thereto.

Further, the medical imaging apparatus 100 may include the communication unit 220. The communication unit 220 may be a component for the medical imaging apparatus 100 to communicate with an internal module or an external device in a wired or wireless manner. The external device may include an external server and a user terminal. The user terminal may include a personal computer (PC), a smartphone, a tablet computer, or a wearable device. The communication unit 220 may include a wired/wireless communication module for accessing a network. For example, as the wireless communication technology, a wireless local area network (WLAN), Wi-Fi, wireless broadband (WiBro), world interoperability for microwave access (WiMAX), high speed downlink packet access (HSDPA), and the like may be used. For example, as the wired communication technology, an x digital subscriber line (xDSL), fiber to the home (FTTH), power-line communication (PLC), and the like may be used. Further, the communication unit 220 may include a short-range communication module to transmit or receive data to or from any device/terminal located in a short range. For example, as the short-range communication technology, Bluetooth, radio-frequency identification (RFID), infrared data association (IrDA), ultra-wideband (UWB), ZigBee, and the like may be used, but the present disclosure is not limited thereto.

Meanwhile, for communication between the workstation 130 and the medical imaging apparatus 100, a high-speed digital interface using low-voltage differential signaling (LVDS) or the like, asynchronous serial communication using a universal asynchronous receiver transmitter (UART) or the like, error synchronous serial communication, or a low-latency network protocol such as a controller area network (CAN) or the like may be used, or various communication methods may be used within the range apparent to those skilled in the art.

The medical imaging apparatus 100 may include the memory 230. The control unit 200 may execute instructions stored in the memory. The memory 230 may be included in the control unit 200 or may be outside the control unit 200. The memory 230 may store various pieces of information related to the medical imaging apparatus 100. For example, the memory 230 may store information related to an operating method of the X-ray source and store a captured image and user authentication information, but the present disclosure is not limited thereto.

The memory 230 may be implemented through a non-volatile storage medium that can continuously store arbitrary data. For example, the memory 230 may include a storage device based on a flash memory and/or a battery-backed memory, as well as a disk, an optical disc, and a magneto-optical storage device, but the present disclosure is not limited thereto. The memory 230 is a main storage device which a processor directly accesses, such as a RAM including a dynamic random-access memory (DRAM), a static random-access memory (SRAM), or the like, and may be a volatile storage device in which information stored therein is instantaneously erased when power is turned off, but the present disclosure is not limited thereto. The memory 230 may be operated by the control unit 200.

Further, the medical imaging apparatus 100 may further include a manipulation unit that provides an interface for manipulation of the medical imaging apparatus 100. The manipulation unit may include the output unit 240 and the input unit 250.

The output unit 240 may output sound or an image that indicates information related to photographing, such as X-ray radiation or the like, under the control of the control unit 200. The output unit 240 may include a speaker or a display. The output unit 240 may output a medical image generated by the control unit 200. The output unit 240 may output a user interface (UI), and information necessary for the user to operate the medical imaging apparatus 100, such as user information or object information. Examples of the output unit 240 may include a speaker, a printer, a cathode ray tube (CRT) display, a liquid crystal display (LCD), a plasma display panel (PDP) display, an organic light-emitting diode (OLED) display, a field-emission display (FED), an LED display, a vacuum fluorescent display (VFD), a digital light processing (DLP) display, a flat-panel display (FPD), a 3D display, a transparent display, etc., or may include various output devices within the range apparent to those skilled in the art.

The workstation 130 and the medical imaging apparatus 100 may be connected to each other in a wireless or wired manner, and the workstation 130 may be present in a space physically separated from the medical imaging apparatus 100.

The workstation 130 may include the storage server 110. The storage server 110 may store a medical image, information on an object, information on a user (medical personnel), and the like. The workstation 130 may include the review device 120. The review device 120 may receive a medical image from the storage server 110 on the basis of the user's command to diagnose the medical image. The workstation 130 and the medical imaging apparatus 100 may transmit, store, process, and output data according to the Digital Imaging and Communications in Medicine (DICOM) standard. Further, the workstation 130 may be a picture archiving and communication system (PACS).

The workstation 130 may include an output unit, an input unit, and a control unit. The output unit and the input unit provide an interface for manipulation of the workstation 130 and the medical imaging apparatus 100 to the user. The control unit of the workstation may control the workstation 130 and the medical imaging apparatus 100.

The medical imaging apparatus 100 may be controlled through the workstation 130, and may be controlled by the control unit 200 included in the medical imaging apparatus 100. Therefore, the user may control the medical imaging apparatus 100 through the workstation 130 or control the medical imaging apparatus 100 through the manipulation unit and the control unit 200, which are included in the medical imaging apparatus 100. In other words, the user may remotely control the medical imaging apparatus 100 through the workstation 130 or may directly control the medical imaging apparatus 100.

The control unit of the workstation 130 and the control unit 200 of the medical imaging apparatus 100 may be provided as separate control units, but the present disclosure is not limited thereto. The control unit of the workstation 130 and the control unit 200 of the medical imaging apparatus 100 may be implemented as one integrated control unit, and the integrated control unit may be included only in one of the workstation 130 and the medical imaging apparatus 100. Hereinafter, the control unit 200 may be the control unit of the workstation 130 and/or the control unit of the medical imaging apparatus 100.

Each of the output unit and the input unit of the workstation 130 and each of the output unit 240 and the input unit 250 of the medical imaging apparatus 100 may provide an interface for manipulation of the medical imaging apparatus 100 to the user. Each of the workstation 130 and the medical imaging apparatus 100 may include an output unit and an input unit, but the present disclosure is not limited thereto. The output unit or the input unit may be implemented only in one of the workstation 130 and the medical imaging apparatus 100.

Hereinafter, the input unit 250 is an input unit of the workstation 130 and/or an input unit of the medical imaging apparatus 100, and the output unit 240 is an output unit of the workstation 130 and/or an output unit of the medical imaging apparatus 100.

The input unit 250 may receive commands for manipulation of the medical imaging apparatus 100 and various types of information related to X-ray photographing from the user. The control unit 200 may control or manipulate the medical imaging apparatus 100 on the basis of the information input to the input unit 250. The input unit 250 may include a joystick, a keyboard, a mouse, a touch screen, a voice recognizer, a fingerprint recognizer, an iris recognizer, or the like, and may include other input devices within the range apparent to those skilled in the art. The user may input a command for X-ray radiation through the input unit 250, and a switch for inputting such a command may be provided in the input unit 250. A radiation command for X-ray radiation may be input to the medical imaging apparatus 100 only when the switch is pressed two times. For example, the switch may have a structure in which, when the user presses the switch, a preparation command for instructing preheating for X-ray radiation is input, and when the user presses the switch deeper while pressing the switch, a radiation command for actual X-ray radiation is input.

That is, the switch may have a structure in which, when the user presses the switch, a preparation command for instructing preheating for X-ray radiation is input, and when the user presses the switch deeper while pressing the switch, a radiation command for actual X-ray radiation is input. When the user manipulates the switch in this way, the control unit 200 generates a signal corresponding to the command, which is input through the switch manipulation, that is, a preparation signal, and transmits the generated signal to the high voltage generator that generates a high voltage.

The high voltage generator receives the preparation signal transmitted from the control unit 200 to start preheating, and when the preheating is completed, the high voltage generator transmits a preparation completion signal to the control unit 200. In addition, the detector also needs to undergo X-ray detection preparation for X-ray detection. The control unit 200 transmits the preparation signal to the detector so that the detector can prepare for detection of the X-rays that have passed through the object while being preheated by the high voltage generator. When the detector receives the preparation signal, the detector prepares for detection of the X-rays, and when the detection preparation is completed, the detector transmits a detection preparation completion signal to the control unit 200.

When the preheating of the high voltage generator is completed and the X-ray detection preparation of the detector is completed, the control unit 200 transmits a radiation signal to the high voltage generator, the high voltage generator generates a high voltage and applies the generated high voltage to the X-ray source, and the X-ray source radiates the X-rays.

When the control unit 200 transmits the radiation signal, the control unit 200 may transmit an output signal such as sound or light to the output unit 240 so that the object can know the X-ray radiation, and may allow predetermined sound or light to be output from the output unit 240. Further, the output unit 240 may output sound or light indicating other information related to photographing other than the X-ray radiation. The output unit 240 may be included in the manipulation unit, but the present disclosure is not limited thereto, and the output unit 240 or a part of the output unit 240 may be positioned at a point different from a point at which the manipulation unit is positioned. For example, the output unit 240 may be positioned on a wall of a photographing room in which X-ray photographing is performed on the object.

The control unit 200 controls the positions of the X-ray radiation unit and the detector, a photographing timing, photographing conditions, and the like according to photographing conditions set by the user.

Specifically, the control unit 200 controls the high voltage generator and the detector according to the command input through the input unit 250 to control photographing setting information such as an X-ray radiation timing, an X-ray intensity, an X-ray radiation area, and the like. Further, the control unit 200 adjusts the position of the detector according to a predetermined photographing condition and controls an operation timing of the detector.

Further, the control unit 200 generates a medical image of the object using image data received through the detector. Specifically, the control unit 200 may receive the image data from the detector to remove noise from the image data, and adjust a dynamic range and interleaving to generate the medical image of the object.

The workstation 130 may further include a communication unit (not illustrated) that can be connected to a server, a medical device, a portable terminal, or the like through a network.

Figure 3:
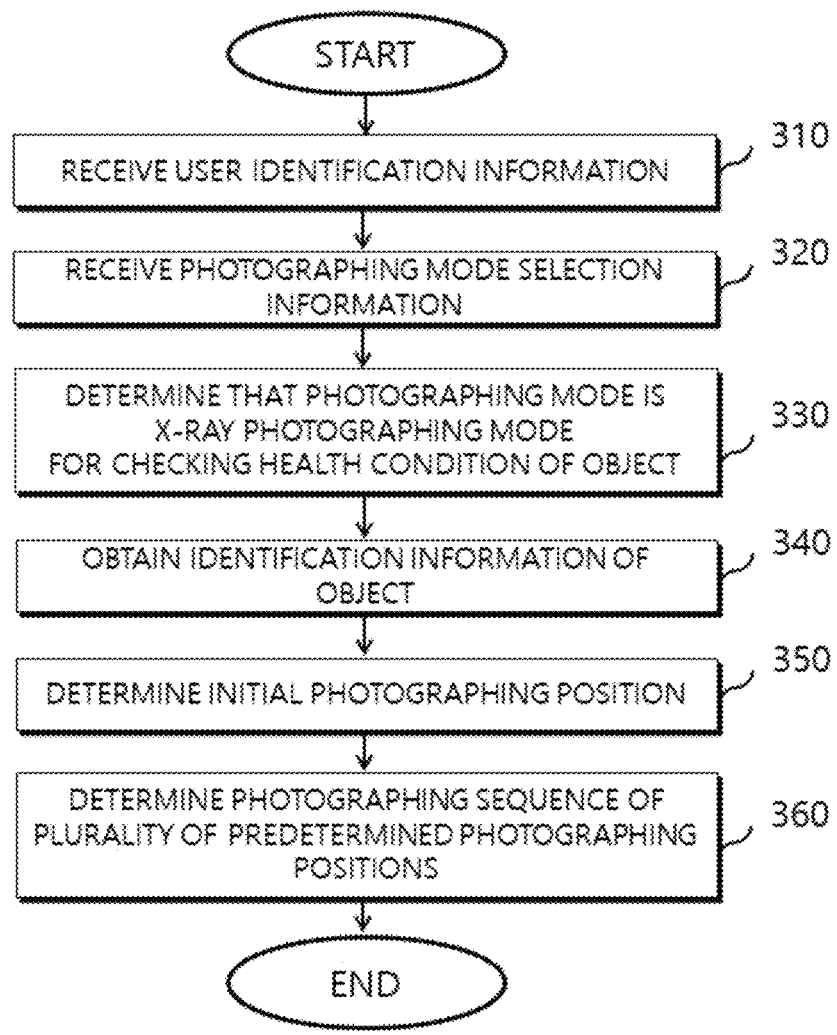
FIG. 3 is a flowchart for describing an operation of a medical imaging apparatus according to an embodiment of the present disclosure.

FIG. 3 is a flowchart for describing an operation of a medical imaging apparatus according to an embodiment of the present disclosure.

A medical imaging apparatus 100 for capturing an X-ray medical image may perform an operation 310 of receiving identification information of a user. The medical imaging apparatus 100 may receive the identification information of the user using the input unit 250. The identification information of the user may include at least one of an identification (ID), a password, a name, a social security number, an email address, fingerprint information, iris information, and a phone number of the user. When the user manipulates the medical imaging apparatus 100, an authentication process may be performed. For example, the medical imaging apparatus 100 may receive an ID and a password of the user through the input unit 250. The medical imaging apparatus 100 may determine whether the received ID and password match an ID and password pre-stored in the memory 230. When it is determined that the received ID and password match the ID and the password pre-stored in the memory 230, the medical imaging apparatus 100 may allow the user to capture a medical image using the medical imaging apparatus 100.

The medical imaging apparatus 100 may perform an operation of receiving photographing mode selection information. The medical imaging apparatus 100 may receive the photographing mode selection information using the input unit 250. The medical imaging apparatus 100 may include a plurality of photographing modes. The plurality of photographing modes may include at least one of a modality worklist (MWL) mode, a non-MWL mode, and a special mode.

The MWL mode is a mode in which photographing proceeds according to a worklist. When the user is authenticated in operation 310, the medical imaging apparatus 100 may obtain a worklist assigned to the corresponding user from a memory or a server. The worklist may include information on an object to be photographed by the user. The worklist may include information on an object or a position of a part of the object to be photographed. The information on the object may include at least one of identification information, a sex, and an age of the object. The object may be, for example, a human, a dog, a cat, or an equine, but the present disclosure is not limited thereto. The identification information of the object may include, for example, at least one of a date of birth, a name, and a sex. The medical imaging apparatus 100 may be controlled to sequentially photograph objects in the worklist. However, the present disclosure is not limited thereto, the medical imaging apparatus 100 may photograph an object selected by the user from among the objects in the worklist. That is, when the object is selected by the user, the medical imaging apparatus 100 may enter a photographing mode. In the case of the MWL mode, since the information on the object is pre-stored, the user may not need to input the information on the object.

The non-MWL mode is a mode in which photographing proceeds without a worklist. When the user selects the non-MWL mode, the medical imaging apparatus 100 may output a UI through which information on an object to be photographed is input. The medical imaging apparatus 100 may receive the information on the object to be photographed from the user through the input unit. Thereafter, the medical imaging apparatus 100 may enter a photographing mode for capturing a medical image of the object.

The special mode is a mode in which a plurality of objects are rapidly photographed. When the special mode is selected, information on the plurality of objects pre-stored in the memory of the medical imaging apparatus 100 may be obtained. Further, the medical imaging apparatus 100 may enter a medical image photographing mode for the plurality of objects. The special mode may be a mode for helping the user rapidly capture a plurality of medical images by simplifying a workflow.

The medical imaging apparatus 100 may include an emergency mode. When the emergency mode is selected, the medical imaging apparatus 100 may immediately enter the photographing mode without obtaining the information on the object.

The medical imaging apparatus 100 may perform an operation 330 of determining that the photographing mode is an X-ray photographing mode for checking a health condition of the object on the basis of at least one of the identification information of the user and the photographing mode selection information.

For example, in the MWL mode, the medical imaging apparatus 100 may derive the worklist on the basis of the received identification information of the user, and when the object included in the worklist needs to be photographed in the X-ray photographing mode for checking the health condition of the object, the medical imaging apparatus 100 may enter the X-ray photographing mode for checking the health condition of the object. Further, in the non-MWL mode, the medical imaging apparatus 100 may receive the information on the object and then enter the X-ray photographing mode for checking the health condition of the object on the basis of the user's input. Further, in the special mode, the medical imaging apparatus 100 may obtain the information on the plurality of objects from the memory and then immediately enter the X-ray photographing mode for checking the health condition of the object. The X-ray photographing mode for checking the health condition of the object is a mode in which a predetermined main part is photographed at multiple angles in order to check the health condition of the object. The user may obtain a plurality of medical images of the object according to the X-ray photographing mode for checking the health condition of the object. For example, when the object is an equine, medical images of a plurality of joints included in legs of the equine, which are captured in at least one direction, may be obtained according to the X-ray photographing mode for checking the health condition of the object. However, since equines are larger and stronger than humans and can get excited during a medical imaging process, it is necessary to stabilize the equine and it is necessary to photograph a plurality of medical images rapidly so that the equine is not uncomfortable.

The medical imaging apparatus 100 may perform an operation 340 of obtaining identification information of the object. For example, as described above, the information on the object may include the identification information of the object. The identification information of the object may be obtained from a server or a memory. Alternatively, the identification information of the object may be input by the user. The identification information of the object may include, for example, at least one of a date of birth, a name, and a sex.

The medical imaging apparatus 100 may determine an operation 350 of determining an initial photographing position from among a plurality of predetermined photographing positions.

FIG. 4 is a diagram showing a plurality of photographing positions according to an embodiment of the present disclosure.

The number of predetermined photographing positions may be 20 or more and 22 or less. Referring to FIG. 4, the plurality of predetermined photographing positions may include a fore fetlock right lateral/medical (LM), a fore carpus right dorsolateeral/palmaromedial (DLPMO), a fore carpus right dorsomedial/palmarolateral oblique (DMPLO), a fore fetlock right dorsopalmar (DP), a hind fetlock right LM, a tarsus right DMPLO, a tarsus right DLPMO, a hind fetlock right DP, a stifle right oblique (OBL), a stifle right caudocranial (CaCr), a fore fetlock left LM, a fore carpus left DLPMO, a fore carpus left DMPLO (or PLDMO), a fore fetlock left DP, a hind fetlock left LM, a tarsus left DMPLO (or PLDMO), a tarsus left DLPMO, a hind fetlock left DP, a stifle left OBL, a stifle left CaCr, and the like. The plurality of predetermined photographing positions may have a sequence. The sequence numbers of FIG. 4 may mean a photographing sequence. However, the present disclosure is not limited thereto. The photographing position may include a body part of the object (equine) and a photographing direction of the body part.

An initial photographing position may be determined based on the user's selection. However, the present disclosure is not limited thereto. The medical imaging apparatus 100 may automatically determine the initial photographing position on the basis of the identification information of the object. Alternatively, the medical imaging apparatus 100 may obtain a predetermined initial photographing position from the memory.

The medical imaging apparatus 100 may select the initial photographing position on the basis of the user's selection as follows. The medical imaging apparatus 100 may display a screen for selecting the initial photographing position. For example, the medical imaging apparatus 100 may display the plurality of photographing positions of FIG. 4. The medical imaging apparatus 100 may obtain selection information on the initial photographing position from the user. The medical imaging apparatus 100 may determine the initial photographing position on the basis of the selection information.

The medical imaging apparatus 100 may obtain an initial photographing position stored in the past from the memory on the basis of the received identification information of the object. In the medical imaging apparatus 100, the identification information of the object, the pre-stored initial photographing position, and information on a state of the object in previous photographing may be stored so as to correspond to each other. The medical imaging apparatus 100 may obtain the pre-stored initial photographing position and the information on the state of the object in the previous photographing on the basis of the identification information of the object. The information on the state of the object in the previous photographing may include at least one of whether a stabilizer is administered, whether food is ingested before photographing, a photographing sequence, and whether an accident occurs. When the information on whether the accident occurs indicates that no accident has occurred, the medical imaging apparatus 100 may determine the pre-stored initial photographing position obtained from the memory as the initial photographing position of operation 350.

Figure 5:
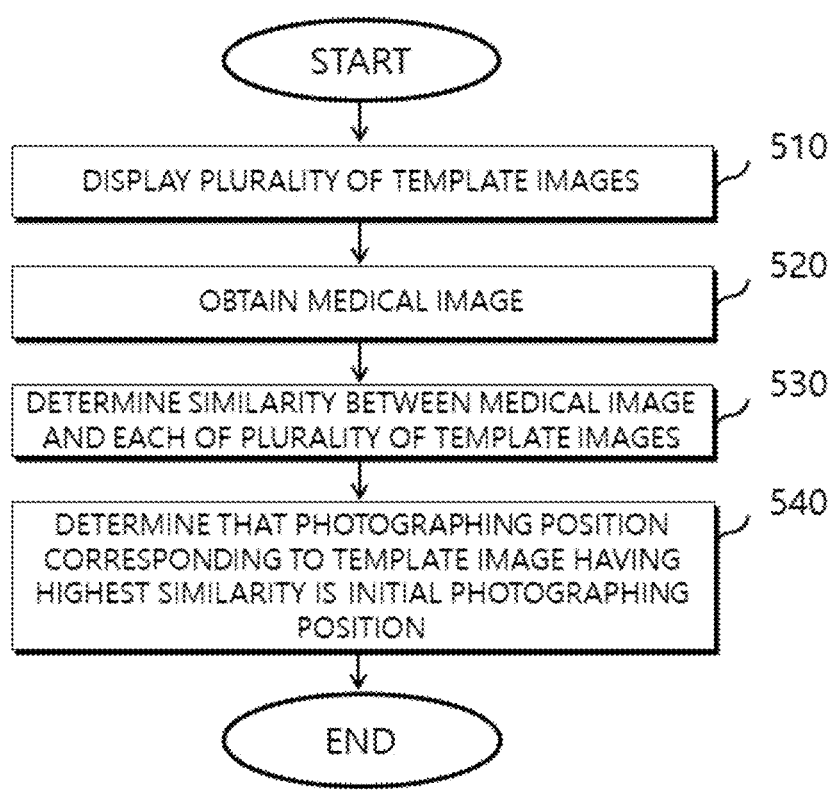
FIG. 5 is a flowchart for describing an operation of a medical imaging apparatus according to an embodiment of the present disclosure.

FIG. 5 is a flowchart for describing an operation of a medical imaging apparatus according to an embodiment of the present disclosure. Further, FIG. 6 shows a screen displayed on a medical imaging apparatus according to an embodiment of the present disclosure.

Figure 6:
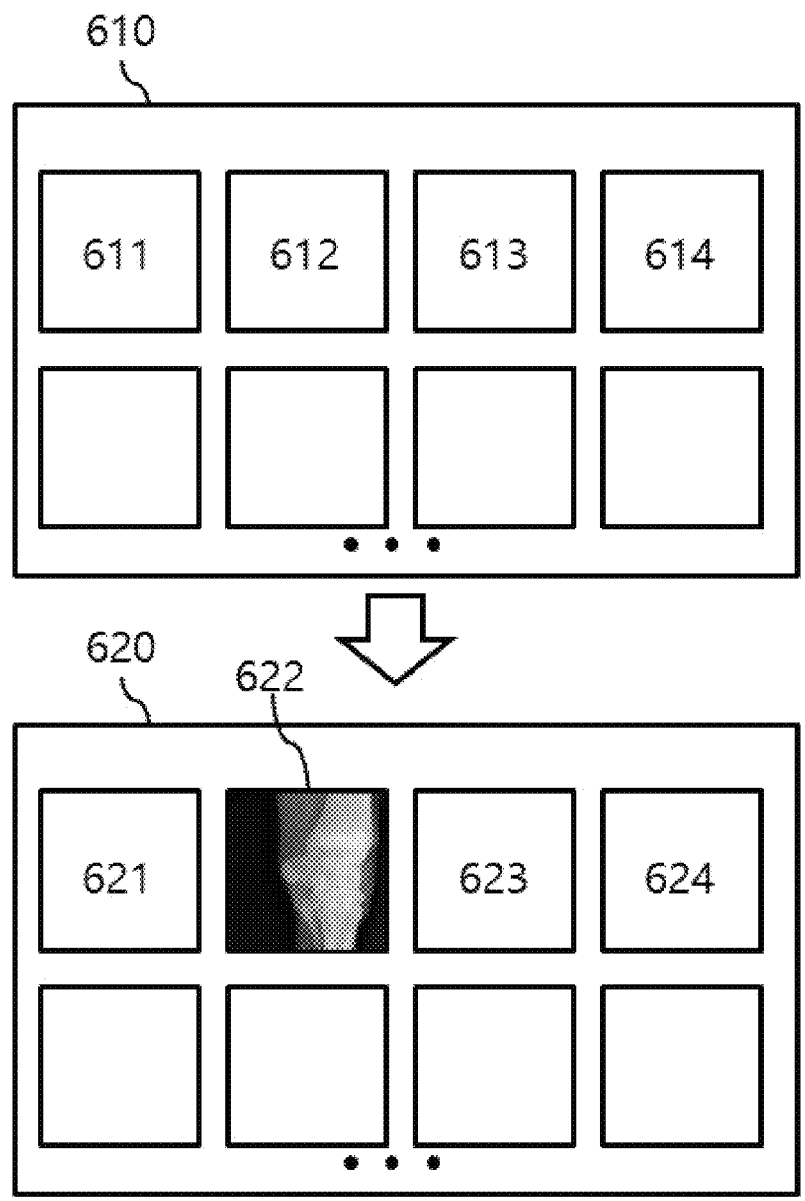
FIG. 6 shows a screen displayed on a medical imaging apparatus according to an embodiment of the present disclosure.

Referring to FIGS. 5 and 6, the medical imaging apparatus 100 may select an initial photographing position on the basis of the user's selection as follows. The medical imaging apparatus 100 may perform an operation 510 of displaying a plurality of template images 611 to 614 for a plurality of predetermined photographing positions. Referring to FIG. 6, the medical imaging apparatus 100 may display the plurality of template images 611 to 614 on a display 610 included in the output unit 240. In FIG. 6, reference numerals are given to a plurality of (four) template images 611 to 614, but the present disclosure is not limited thereto. The number of template images 611 to 614 may be 20 or more and 22 or less. One of the plurality of template images may include information on apart of an object, information on a position of a detector with respect to the part of the object, and information on a position of a source.

The medical imaging apparatus 100 may perform an operation 520 of obtaining a medical image on the basis of the user's input. As described above, the user may input the X-ray irradiation command to the medical imaging apparatus 100 through the input unit 250. The medical imaging apparatus 100 may capture a medical image on the basis of the user's input. The obtained medical image may correspond to one of the plurality of template images 611 to 614.

The medical imaging apparatus 100 may perform an operation 530 of determining the similarity between the obtained medical image and each of the plurality of template images 611 to 614. The medical imaging apparatus 100 may use an algorithm such as a scale-invariant feature transform (SIFT), a histogram of oriented gradients (HOG), Haar, Ferns, a local binary pattern (LBP), or a modified census transform (MCT) to determine the similarity between images.

Further, the medical imaging apparatus 100 may determine the similarity between the images using an artificial neural network or a machine learning model. The machine learning model may be a model obtained by machine-learning whether the medical image is the same as one of the plurality of template images. The machine learning model may be pre-trained by the server. More specifically, in the server, a past medical image and a flag indicating whether the past medical image is the same as one of the plurality of template images may be stored. The flag may be written by the user. For example, the flag may have a value of 1 when the past medical image is captured at the same position as one template image, and a value of 0 when the past medical image is captured at a different position from one template image. The server may generate a machine learning model using a convolutional neural network (CNN). The server may machine-learn a correlation between the past medical image and the flag. The number of machine learning models generated by the server may be the same as the number of plurality of template images. The server may generate a plurality of machine learning models by different flags for each machine learning model. The plurality of machine learning models may correspond to the plurality of template images in one-to-one correspondence. The medical imaging apparatus 100 may determine whether the medical image is the same as one of the plurality of template images using the plurality of machine learning models. Since the medical imaging apparatus 100 uses the plurality of machine learning models, the medical imaging apparatus 100 may determine that one medical image corresponds to the plurality of template images. In this case, the medical imaging apparatus 100 may obtain a probability that the medical image corresponds to one template image for each machine learning model. The probability that the medical image corresponds to one template image may be an output value of an output layer included in the machine learning model. The medical imaging apparatus 100 may select a machine learning model with the highest probability that the medical image corresponds to one template image. The medical imaging apparatus 100 may determine that the template image corresponding to the selected machine learning model corresponds to the medical image.

Further, the medical imaging apparatus 100 may determine the similarity between images using an artificial neural network or a machine learning model. The machine learning model may be a model obtained by machine-learning which template image the medical image is classified into among the plurality of template images. The machine learning model may be pre-trained by the server. More specifically, in the server, the past medical image and type information of the template image corresponding to the past medical image may be stored. For example, when the number of types of template images is 20, the type information of the template image may have 0 to 19. The type information of the template image may be written by the user. The server may generate a machine learning model using a CNN. The server may machine-learn a correlation between the past medical image and the type information of the template image. The number of machine learning models generated by the server may be one. The medical imaging apparatus 100 may apply the medical image to the machine learning model to output the type information of the template image corresponding to the medical image. That is, the medical imaging apparatus 100 may output a type of a template image having the highest similarity to the medical image.

The medical imaging apparatus 100 may perform an operation 540 of determining a photographing position corresponding to a template image having the highest similarity among a plurality of template images as an initial photographing position. The medical imaging apparatus 100 may output the photographing position corresponding to the template image having the highest similarity among the plurality of template images. When information indicating user approval is received, the medical imaging apparatus 100 may determine the photographing position corresponding to the template image having the high similarity as the initial photographing position.

The medical imaging apparatus 100 may replace a template image 622 corresponding to a medical image among a plurality of template images 621 to 624 with the medical image as shown on a display 620 of FIG. 6. As described above, after the template image 622 corresponding to the medical image among the plurality of template images 621 to 624 is replaced with the medical image, the plurality of template images 621 to 624 may be arranged while operations 360 and 810 are performed.

Referring to FIG. 3 again, the medical imaging apparatus 100 may perform an operation 360 of determining the photographing sequence of the plurality of predetermined photographing positions on the basis of the initial photographing position. For example, in the medical imaging apparatus 100, the photographing sequence of the plurality of photographing positions corresponding to the initial photographing position may be pre-stored. Accordingly, when the initial photographing position is determined, the medical imaging apparatus 100 may determine the photographing sequence of the plurality of photographing positions on the basis of the initial photographing position. However, the present disclosure is not limited thereto. The medical imaging apparatus 100 may determine the photographing sequence on the basis of one table 400 as shown in FIG. 4. When the initial photographing position is determined, the medical imaging apparatus 100 may determine the photographing sequence from the photographing position corresponding to the initial photographing position according to the sequence described in the table 400. Further, the photographing sequence may be determined so that photographing is performed at a photographing position corresponding to sequence number 1 of the order of the table 400 after photographing is performed at a photographing position corresponding to the last sequence number (sequence number 20) of the order of the table 400. For example, when the initial photographing position is the "tarsus right DMPLO," which is sequence number 6, the medical imaging apparatus 100 may determine the photographing sequence in the order of sequence number 6 to sequence number 20, or sequence number 1 to sequence number 5. Further, the medical imaging apparatus 100 may determine the photographing sequence on the basis of the user's input. The user may input photographing plan information to the medical imaging apparatus 100 before capturing the medical image of the object. The photographing plan information may include at least one of the initial photographing position and the photographing sequence. The medical imaging apparatus 100 may preferentially use the photographing sequence based on the user's input instead of the pre-stored photographing sequence. Further, the medical imaging apparatus 100 may determine the photographing sequence on the basis of the user's input during photographing. That is, the photographing sequence may be changed in real time on the basis of the user's input.

The determined photographing sequence may be a sequence in which the user captures an image while moving around the object in a clockwise or counterclockwise direction. However, the present disclosure is not limited thereto.

The determined photographing sequence may be a sequence in which the user's movement is minimized and thus a medical image can be captured the fastest. Since the user needs to move the medical imaging apparatus to capture the medical image, minimizing the user's movement may mean that the user's fatigue is minimized.

The medical imaging apparatus 100 may perform the following process to determine the photographing sequence.

Figure 7:
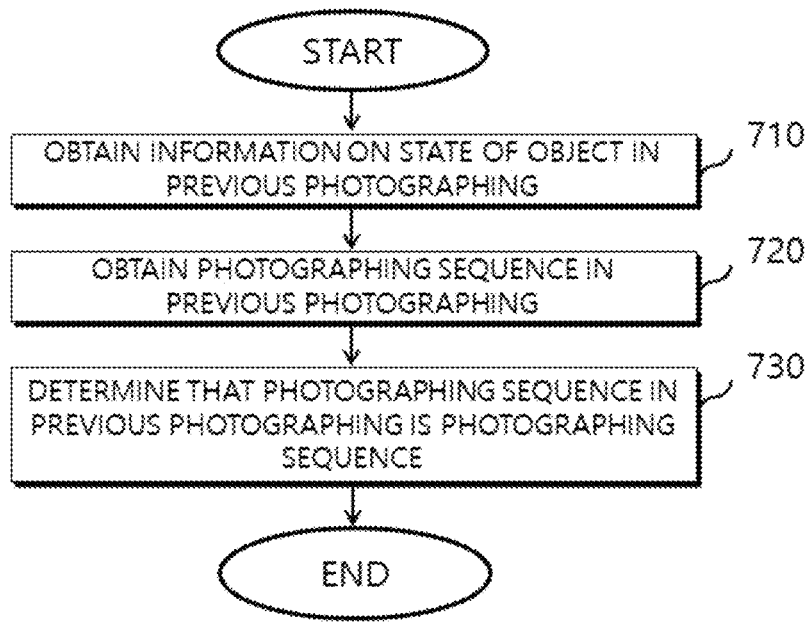
FIG. 7 is a flowchart showing an operation of a medical imaging apparatus according to an embodiment of the present disclosure.

FIG. 7 is a flowchart showing an operation of a medical imaging apparatus according to an embodiment of the present disclosure.

The medical imaging apparatus 100 may perform an operation 710 of obtaining information on a state of an object in previous photographing on the basis of identification information of the object. A health condition of an equine (object) may need to be checked periodically. Therefore, a medical image of the object may have previously captured. In the medical imaging apparatus 100 or the workstation 130, the information on the state of the object in the previous photographing may be stored. The medical imaging apparatus 100 or the workstation 130 may receive and store the information on the state of the equine (object) during photographing after capturing all the medical images in the previous photographing.

The information on the state of the object may include at least one of whether a stabilizer is administered, whether food is ingested before photographing, a type of ingested food, a photographing sequence, and whether an accident occurs. Whether the stabilizer is administered may indicate whether the stabilizer has been administered during the previous photographing of the object. Additionally, the information on the state of the object may include a type and amount of the administered stabilizer.

Whether the food is ingested before photographing may indicate whether the object has ingested the food before photographing. The information on the state of the object may additionally include a type of ingested food and a period of time from the ingestion of the food to the previous photographing.

The photographing sequence may be a photographing sequence of the plurality of photographing positions used in the previous photographing.

Whether the accident occurs may indicate whether a photographer (user) is injured by the object during photographing. However, the present disclosure is not limited thereto, and whether the accident occurs may simply indicate whether the equine is excited. The information on the state of the object may additionally include a period of time from a start of photographing to a time of the accident.

Further, the information on the state of the object may further include whether the object (equine) has a disease during photographing or a type of the disease.

When the information on whether an accident occurs, which is included in the information on the state of the object in the previous photographing, indicates that no accident has occurred, the medical imaging apparatus 100 may perform an operation 720 of obtaining a photographing sequence in the previous photographing included in the information on the state of the object in the previous photographing. The medical imaging apparatus 100 may perform an operation 730 of determining the photographing sequence in the previous photographing as a photographing sequence. That is, the medical imaging apparatus 100 may perform photographing using the photographing sequence in which photographing was previously successful without an accident. Since the equine (object) is a sensitive animal, the equine (object) may sensitively react when photographing proceeds in a specific sequence. However, when photographing proceeds in a photographing sequence in which the equine (object) feels comfortable, a photographing success rate may be increased.

Figure 8:
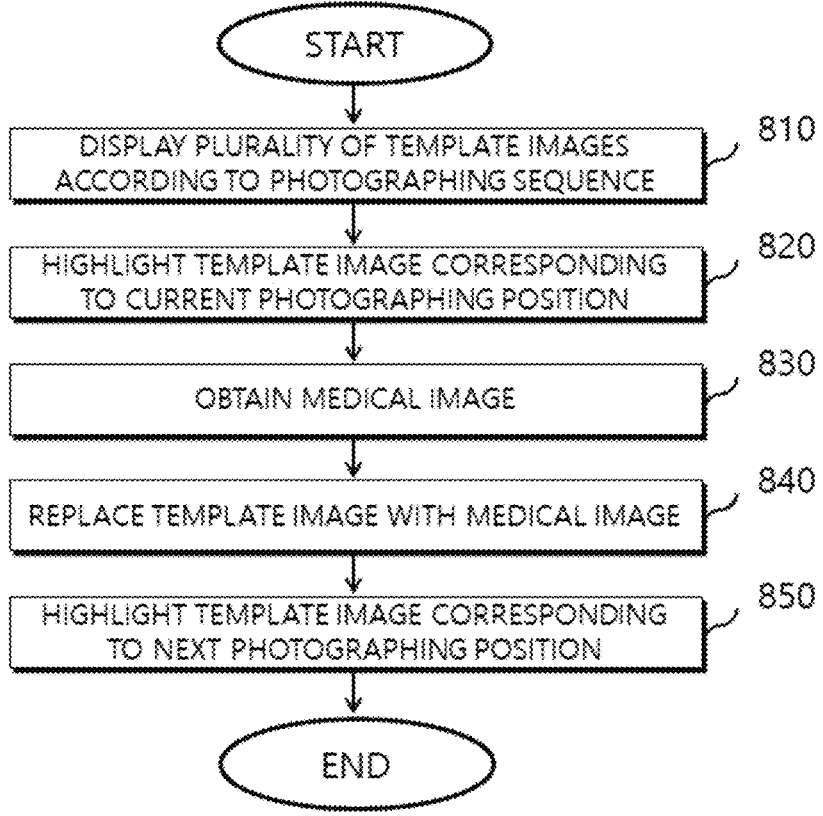
FIG. 8 is a flowchart for describing an operation method of a medical imaging apparatus according to an embodiment of the present disclosure.
Figure 9:
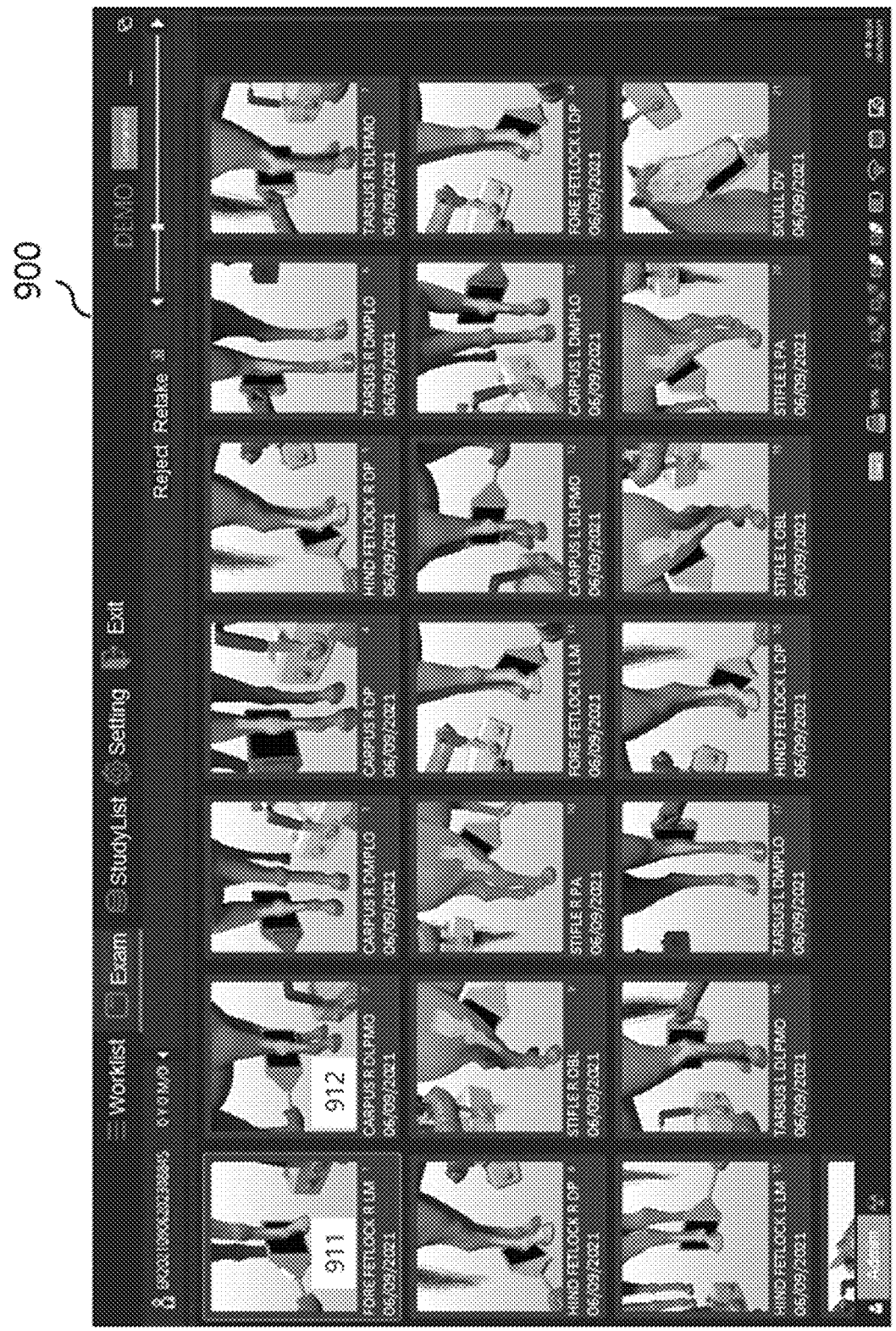
FIG. 9 shows images for describing an operation of a medical imaging apparatus according to an embodiment of the present disclosure.
Figure 10:
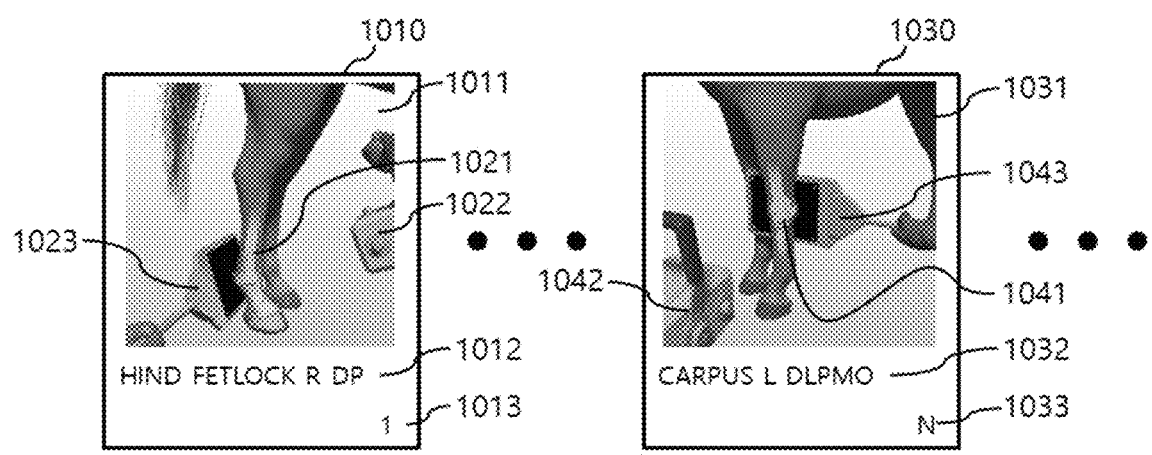
FIG. 10 shows images for describing an operation of a medical imaging apparatus according to an embodiment of the present disclosure.

FIG. 8 is a flowchart for describing an operation method of a medical imaging apparatus according to an embodiment of the present disclosure. FIG. 9 shows images for describing an operation of a medical imaging apparatus according to an embodiment of the present disclosure. FIG. 10 shows images for describing an operation of a medical imaging apparatus according to an embodiment of the present disclosure.

The following process may be performed after the operation 360 of determining the photographing sequence of the plurality of predetermined photographing positions of FIG. 3 is performed.

The medical imaging apparatus 100 may determine whether the medical image of the object has been captured in the past on the basis of the identification information of the object. When the medical image corresponding to the identification information of the object is stored in the workstation 130 or the medical imaging apparatus 100, the medical imaging apparatus 100 may determine that the medical image of the object has been captured in the past.

When it is determined that the medical image of the object has been captured in the past, the medical imaging apparatus 100 may obtain information on a past state of the object from the memory of the workstation 130 or the medical imaging apparatus 100. The information on the past state of the object may include at least one of whether a stabilizer is administered, whether food is ingested before photographing, a type of ingested food, a photographing sequence, and whether an accident occurs. The medical imaging apparatus 100 may output the information on the past state of the object. The user may compare the output information on the past state of the object to information on a current state of the object. For example, when whether the accident occurs, which is included in the information on the past state of the object, indicates that no accident has occurred, the user may follow the information on the past state of the object as much as possible. Further, when whether the accident occurs, which is included in the information on the past state of the object, indicates that an accident has occurred, the user may try to change at least one piece of the information on the past state of the object as much as possible.

The medical imaging apparatus 100 may automatically predict whether an accident occurs. The medical imaging apparatus 100 may obtain the information on the current state of the object. For example, the medical imaging apparatus 100 may obtain whether a stabilizer is administered, whether food is ingested before photographing, a type of ingested food, and a photographing sequence through the input unit 250 or the memory. The medical imaging apparatus 100 may compare the information on the current state of the object to the information on the past state of the object to predict whether an accident occurs. For example, as the information on the current state of the object is similar to the information on the past state of the object, the occurrence of an accident can be predicted.

When whether the accident occurs, which is included in the information on the past state of the object, indicates that no accident has occurred, the following process may be performed. The medical imaging apparatus 100 may predict the probability of occurrence of an accident to be low as the information on the current state of the object matches the information on the past state of the object, and may predict the probability of occurrence of an accident to be high as the information on the current state of the object does not match the information on the past state of the object. The user may be careful not to cause an accident on the basis of the probability of occurrence of an accident predicted by the medical imaging apparatus 100. Therefore, the user may safely obtain the medical image.

When whether the accident occurs, which is included in the information on the past state of the object, indicates that an accident has occurred, the medical imaging apparatus 100 may not use the corresponding information on the past state of the object to predict whether the accident has occurred.

Referring to FIG. 8, the medical imaging apparatus 100 may perform an operation 810 of displaying a plurality of template images for a plurality of predetermined photographing positions according to a photographing sequence. For example, the medical imaging apparatus 100 may display the plurality of template images for the plurality of predetermined photographing positions on a screen 900 shown in FIG. 9. The screen 900 may be divided into a plurality of regions 911 and 912. Each of the plurality of regions 911 and 912 may include one template image. The plurality of template images may be arranged from left to right in a first row, from left to right in a second row, and from left to right in an $M^{th}$ row according to the photographing sequence. However, the present disclosure is not limited thereto. M may be a natural number.

FIG. 10 shows images showing some of the plurality of regions 911 and 912 shown in FIG. 9. A plurality of regions 1010 and 1030 of FIG. 10 may correspond to the plurality of regions 911 and 912 of FIG. 9, respectively. Referring to FIG. 10, a template image 1011 may be a medical image captured in the past. Template images may correspond to a plurality of photographing positions in one-to-one correspondence. The template image 1011 may correspond to one of the plurality of photographing positions. The template image 1011 may be an image for identification information of the same object, or may be images of identification information of different objects. That is, the template image 1011 may include medical images for different equines (objects). The template image 1011 may indicate a representative medical image for one photographing position among a plurality of photographing positions. The template image 1011 may be a past medical image of a current object to be photographed. However, the present disclosure is not limited thereto. The user may approximatively predict a shape of an image to be captured in the future by referring to the image captured in the past. Further, when the currently captured image is too different from the template image, photographing may be performed again.

The medical imaging apparatus 100 may display the plurality of regions 1010 and 1030. One template image 1011 among the plurality of template images may be displayed on the region 1010. One template image 1011 among the plurality of template images may include information 1021 on a part of the object, information 1023 on a position of a detector with respect to the part of the object, and information 1022 on a position of a source. As shown in FIG. 10, the information 1021 on the part of the object, the information 1023 on the position of the detector with respect to the part of the object, and the information 1022 on the position of the source may be displayed as images or text. The information 1021 on the part of the object, the information 1023 on the position of the detector with respect to the part of the object, and the information 1022 on the position of the source may be displayed as 2D images or 3D images. The information 1021 on the part of the object is information corresponding to the photographing position, and may include information on a body part of the object for which a medical image is to be captured. The information 1023 on the position of the detector with respect to the part of the object may indicate at what angle and in which direction the detector should be positioned with respect to which body part of the object. The information 1022 on the position of the source may indicate at what angle and in which direction the source should be positioned with respect to which body part of the object.

The positions of the source and the detector may be the same as the DP, the DLPMO, the LM, the PLDMO, the PD, the PMDLO, the ML, and the DMPLO. The DP may indicate that the source is placed in front of the object and the detector is placed behind the object. The LM may indicate that the source is placed outside the object and the detector is placed inside the object. The PD may indicate that the source is placed behind the object and the detector is placed in front of the object. The ML may indicate that the source is placed inside the object and the detector is placed outside the object. The positions of the source and the detector of the DLPMO may be positions between the DP and the LM, the positions of the source and the detector of the PLDMO may be positions between the LM and the PD, the positions of the source and the detector of the PMDLO may be positions between the PD and the ML, and the positions of the source and the detector of the DMPLO may be positions between the ML and the DP.

The user may easily know where the source and the detector are placed on the equine (object) and in what direction to photograph the X-ray only by looking at the template image 1011.

The medical imaging apparatus 100 may display the information 1021 on the part of the object, the information 1023 on the position of the detector with respect to the part of the object, and the information 1022 on the position of the source on a lower end of the region 1010 as text 1012. Further, the medical imaging apparatus 100 may display the photographing sequence of the template image 1011 on the lower end of the region 1010 as text 1013. Based on the information 1021 on the part of the object, the information 1023 on the position of the detector with respect to the part of the object, the information 1022 on the position of the source, and the photographing sequence, which are displayed as the text 1012 and 1013, the user may easily recognize what the current photographing sequence is.

One template image 1031 among the plurality of template images may be displayed in the region 1030. One template image 1031 among the plurality of template images may include information 1041 on the part of the object, information 1043 on the position of the detector with respect to the part of the object, and information 1042 on the position of the source. As shown in FIG. 10, the information 1041 on the part of the object, the information 1043 on the position of the detector with respect to the part of the object, and the information 1042 on the position of the source may be displayed as images or text. The information 1041 on the part of the object is information corresponding to the photographing position, and may include information on a body part of the object for which a medical image is to be captured. The information 1043 on the position of the detector with respect to the part of the object may indicate at what angle and in which direction the detector should be positioned with respect to which body part of the object. The information 1042 on the position of the source may indicate at what angle and in which direction the source should be positioned with respect to which body part of the object.

The medical imaging apparatus 100 may display the information 1041 on the part of the object, the information 1043 on the position of the detector with respect to the part of the object, and the information 1042 on the position of the source on a lower end of the region 1030 as the text 1032. Further, the medical imaging apparatus 100 may display the photographing sequence of the template image 1031 on the lower end of the region 1030 as the text 1033.

Referring to FIG. 8 again, the medical imaging apparatus 100 may perform an operation 820 of highlighting the template image corresponding to the current photographing position on the basis of the photographing sequence. Referring to FIG. 9, it can be seen that a border of the region 911 is displayed darker than a border of the region 912. As described above, the medical imaging apparatus 100 may highlight the template image corresponding to the current photographing position on the basis of the photographing sequence. The medical imaging apparatus 100 may emphasize the border to highlight the template image, and display the border brighter than other template images or display text or an icon near the template image.

The medical imaging apparatus 100 may perform an operation 830 of obtaining a medical image on the basis of the user's input. The medical imaging apparatus 100 may control the source and the detector on the basis of a signal from a manipulation unit to capture the medical image. The captured medical image may correspond to the current photographing position.

The medical imaging apparatus 100 may perform an operation 840 of replacing the template image corresponding to the photographing position of the medical image with the medical image. Since the template image is an image displayed to guide the user's photographing, the medical imaging apparatus 100 may display the captured medical image without displaying the template image for the photographing position where photographing is completed. The user may easily know the photographing position where photographing has been completed and the photographing position where the photographing is to be performed.

The medical imaging apparatus 100 may perform an operation 850 of highlighting the template image corresponding to the next photographing position after the current photographing position on the basis of the photographing sequence. Therefore, the user may easily grasp the next photographing position after the current photographing position. As described above, the medical imaging apparatus 100 may help the user to rapidly obtain the plurality of medical images of the object by guiding the photographing sequence.

Figure 11:
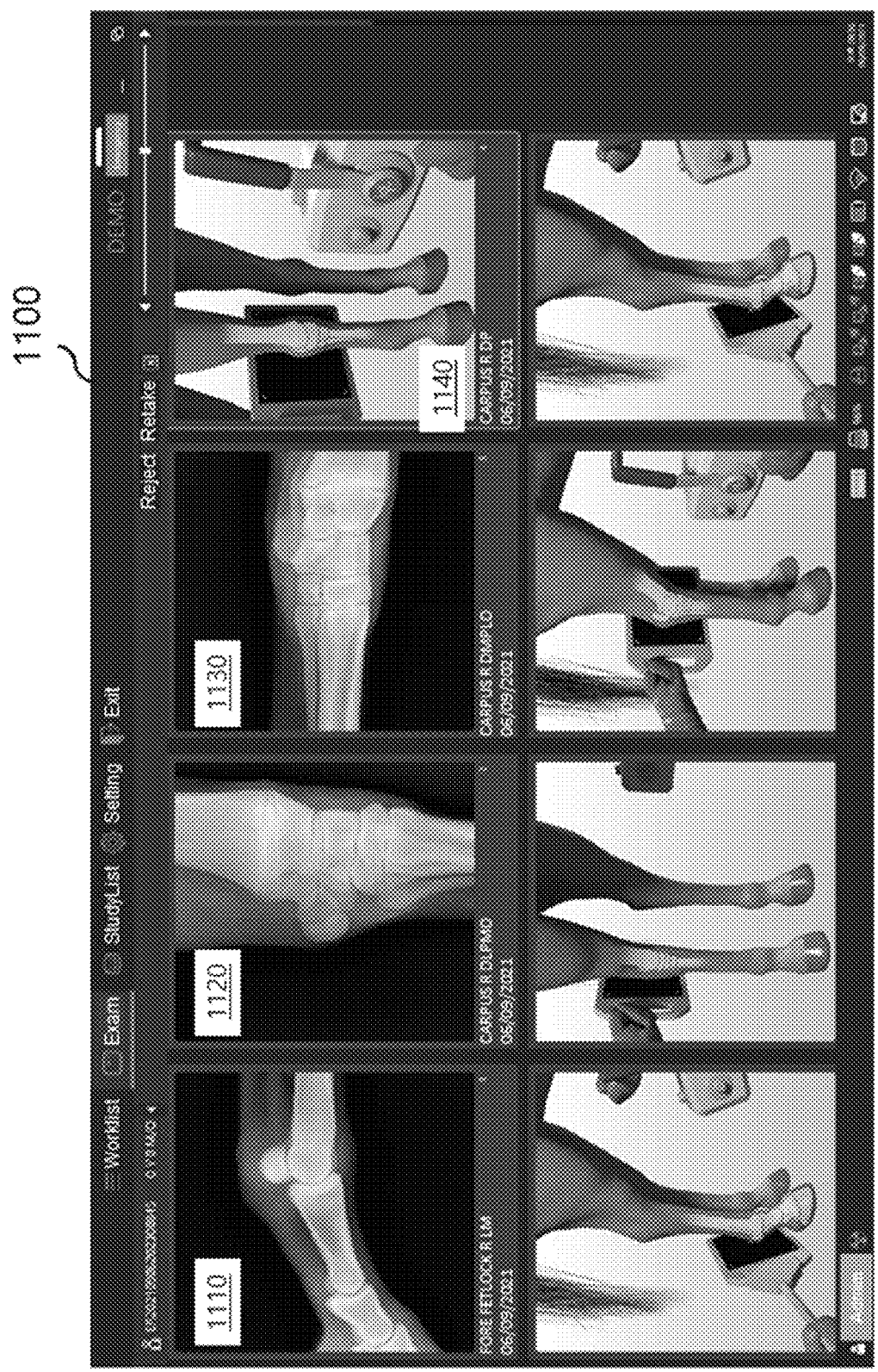
FIG. 11 shows images for describing an operation of a medical imaging apparatus according to an embodiment of the present disclosure.

FIG. 11 shows images for describing an operation of a medical imaging apparatus according to an embodiment of the present disclosure.

A screen 1100 may be displayed on the medical imaging apparatus 100. A region 1110, a region 1120, and a region 1130 may be photographing parts where the medical image capturing is completed. Therefore, in operation 840, template images corresponding to the region 1110, the region 1120, and the region 1130 may be replaced with medical images corresponding to the region 1110, the region 1120, and the region 1130, respectively. The medical image may include at least one of an X-ray image, an ultrasound image, an MRI image, and a CT image. Further, as in operation 850, a region 1140 corresponding to the next photographing position may be highlighted.

Figure 12:
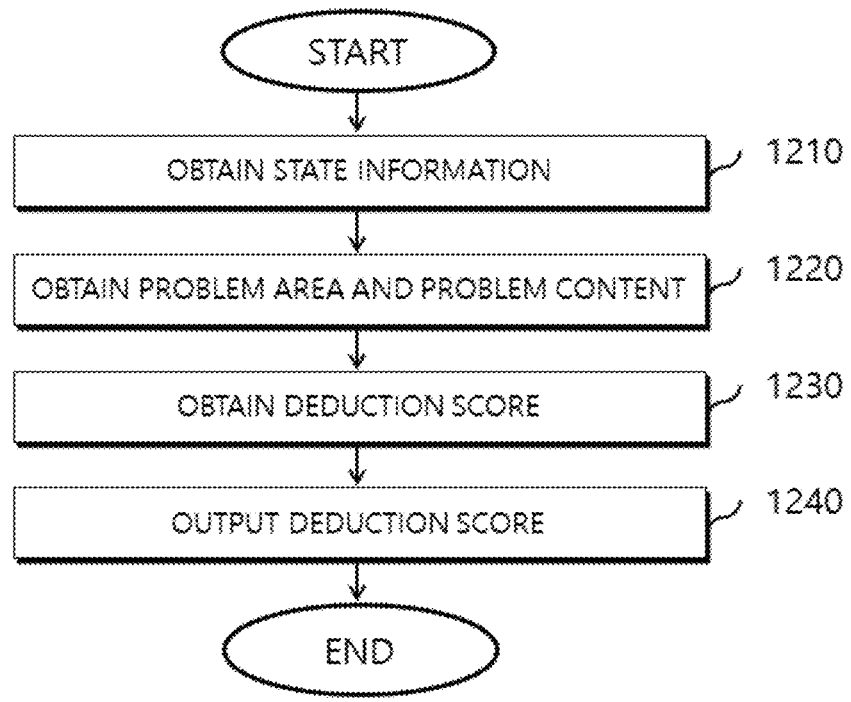
FIG. 12 is a flowchart for describing an operation of a medical imaging apparatus according to an embodiment of the present disclosure.

FIG. 12 is a flowchart for describing an operation of a medical imaging apparatus according to an embodiment of the present disclosure.

Operations of FIG. 12 may be performed after the operation 840 is completed. The operations of FIG. 12 may be performed after all the medical images for the plurality of photographing positions are obtained. However, the operations of FIG. 12 may be performed after the medical image for one photographing position among the plurality of photographing positions is obtained.

The medical imaging apparatus 100 may perform an operation 1210 of obtaining diagnostic information on the medical image from the user. The medical imaging apparatus 100 may obtain the diagnostic information through the input unit 250. More specifically, the medical imaging apparatus 100 may provide a UI for inputting the diagnostic information. The medical imaging apparatus 100 may provide at least one icon indicating problem content. The user may select an icon corresponding to the problem content. Further, the user may drag the icon corresponding to the problem content from the medical image to a problem area. Alternatively, the user may click or touch the problem area to display the icon corresponding to the problem content at a corresponding position. The problem content may include at least one of incontinence, a fracture, and a cure after a fracture.

The medical imaging apparatus 100 may perform an operation 1220 of obtaining the problem area and the problem content included in the diagnostic information. That is, according to operation 1210, the user may display the icon corresponding to the problem content on the medical image. The medical imaging apparatus 100 may obtain the problem content and the problem area on the basis of the medical image on which the icon is displayed. For example, the medical imaging apparatus 100 may determine the problem content on the basis of a type of the icon. Further, the medical imaging apparatus 100 may determine the problem area on the basis of the photographing position corresponding to the medical image. Further, the medical imaging apparatus 100 may determine which bone among one or more bones included in one medical image has a problem. The medical imaging apparatus 100 may determine which bone has a problem using a rule-based learning model or a machine learning model.

Further, the medical imaging apparatus 100 may determine which bone has a problem using an artificial neural network or a machine learning model. The machine learning model may be a model in which bone has a problem is determined based on the medical image on which an icon is displayed through machine learning. The machine learning model may be pre-trained by the server. More specifically, in the server, a past medical image on which an icon is displayed and identification information of a bone with a problem corresponding to the past medical image may be stored. For example, when there are five types of bones in the medical image, the identification information of the bone with the problem may have 0 to 4. The identification information of the bone with the problem may be written by the user. The server may generate a machine learning model using a CNN. The server may machine-learn a correlation between the past medical image on which the icon is displayed and the identification information of the bone with the problem. There may be only one machine learning model generated by the server. The medical imaging apparatus 100 may receive the machine learning model from the server. The medical imaging apparatus 100 may receive the machine learning model from the server. The medical imaging apparatus 100 may output the identification information of the bone with the problem corresponding to the medical image by applying the medical image on which the icon is displayed to the machine learning model.

Further, the medical imaging apparatus 100 may use an artificial neural network or a machine learning model to determine which bone has a problem as well as determine the problem content. The machine learning model may be a model in which bone has a problem is determined based on the medical image through machine learning. The machine learning model may be pre-trained by the server. More specifically, in the server, the past medical image, the identification information of the problem content corresponding to the past medical image, and the identification information of the bone with the problem may be stored. A combination of the identification information of the problem content and the identification information of the bone with the problem may be called classification identification information. For example, when there are five types of bones in the medical image and there are three problem contents, the number of branches into which the medical image can be classified may be 5×3=15 types. That is, the number of branches of the classification identification information may be 15. The medical imaging apparatus 100 may classify the medical image as one of 15 types. The problem content and the identification information of the bone with the problem may be written by the user. The server may generate a machine learning model using a CNN. The server may machine-learn a correlation between the past medical image and the classification identification information. There may be only one machine learning model generated by the server. The medical imaging apparatus 100 may receive the machine learning model from the server. The medical imaging apparatus 100 may receive the machine learning model from the server. The medical imaging apparatus 100 may output the problem content corresponding to the medical image and the bone with the problem by applying the medical image to the machine learning model.

The medical imaging apparatus 100 may perform an operation 1230 of obtaining a deduction score on the basis of the problem area and the problem content. The medical imaging apparatus 100 may store the deduction score for the problem area and the problem content in a table. The medical imaging apparatus 100 may obtain the deduction score on the basis of the table. The medical imaging apparatus 100 may store the deduction score for the problem content and the bone with the problem in a table. The medical imaging apparatus 100 may obtain the deduction score on the basis of the table.

The medical imaging apparatus 100 may further perform the following process when performing the operation 1230 of obtaining the deduction score. When the medical imaging apparatus 100 obtains the same diagnostic information from different medical images obtained by capturing the same part of the object at different angles, the medical imaging apparatus 100 may perform an operation of obtaining of the deduction score using only diagnostic information on one medical image among the different medical images. For example, when a medical image at an LM and a medical image at a DP are captured for an ankle of a left forelimb of an equine (object) and a fracture is found on the medical image at the LM and the medical image at the DP, the medical imaging apparatus 100 may determine the deduction score using one of the medical image at the LM and the medical image at the DP.

The medical imaging apparatus 100 may perform an operation 1240 of outputting the deduction score. Further, in the medical imaging apparatus 100, metadata of the medical image may be stored. Later, a reviewer may obtain the stored deduction score together with the medical image. The medical imaging apparatus 100 may objectively determine the cause of the deduction without being biased. Therefore, the reviewer may determine a state of the equine (object) more objectively by checking the deduction score of the medical imaging apparatus 100.

Figure 13:
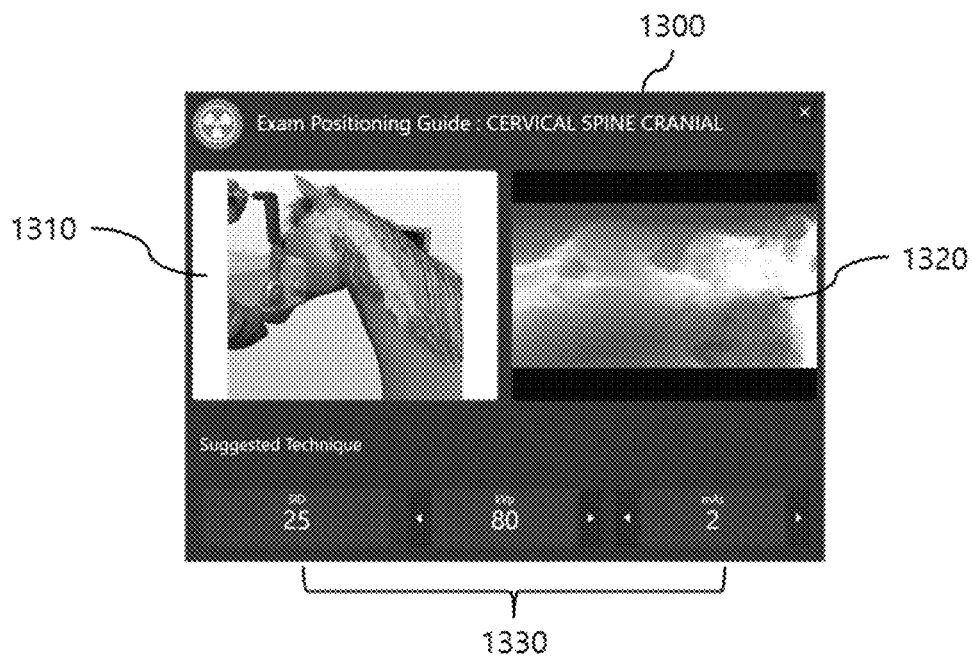
FIG. 13 shows a screen displayed on a medical imaging apparatus according to an embodiment of the present disclosure.

FIG. 13 shows a screen displayed on a medical imaging apparatus according to an embodiment of the present disclosure.

The medical imaging apparatus 100 may further perform the following process when performing the operation 820 of highlighting the template image corresponding to the current photographing position or the operation 830 of obtaining the medical image. The medical imaging apparatus 100 may display a screen 1300. The medical imaging apparatus 100 may output a template image 1310 including information on a part of an object, information on a position of a detector with respect to the part of the object, and information on a position of a source. Further, the medical imaging apparatus 100 may output a template image 1320 including a medical image captured in the past. The user may know a method of obtaining a medical image by referring to the template images 1310 and 1320, and may predict a medical image to be obtained. Further, the medical imaging apparatus 100 may obtain photographing setting information 1330 of the medical imaging apparatus on the basis of the photographing part. The photographing setting information 1330 may include a distance (SID) between the source and the detector, a maximum electrical potential (kVp) across an X-ray tube (source), and a current (mAs) of the X-ray tube (source). In the medical imaging apparatus 100, the photographing setting information 1330 corresponding to each of the plurality of photographing positions may be stored. The medical imaging apparatus 100 may obtain and apply the photographing setting information 1330 corresponding to the current photographing position. The medical imaging apparatus 100 may obtain and apply the photographing setting information 1330 from the memory whenever the photographing position is changed. Further, the medical imaging apparatus 100 may obtain the photographing setting information 1330 on the basis of the identification information of the object. For example, when the object has been photographed by the medical imaging apparatus 100 in the past, the photographing setting information used in past photographing may be stored in the medical imaging apparatus 100 to correspond to the identification information of the object. The medical imaging apparatus 100 may obtain and apply the photographing setting information for each past photographing part from the memory on the basis of the identification information of the object.

Equines (objects) have thick muscles and thin parts, and thus it is necessary to set photographing setting information differently for each part to be photographed. Further, since body sizes of the equines (objects) are different for each breed, it is necessary to set the photographing setting information differently according to the identification information of the object. Since the medical imaging apparatus 100 of the present disclosure automatically changes the photographing setting information, user manipulation may be reduced and the medical image may be rapidly captured.

The medical imaging apparatus 100 may further perform the following process when performing the operation 840 of replacing the template image with the medical image.

The medical imaging apparatus 100 may perform an operation of converting the medical image obtained in operation 830 into a black-and-white image. When a value of a pixel of the medical image is less than or equal to a first threshold value, the medical imaging apparatus 100 may determine the value of the pixel to be 0. Further, when the value of the pixel of the medical image is greater than or equal to a second threshold value, the medical imaging apparatus 100 may determine the value of the pixel to be a maximum value. The maximum value of the pixel may be determined based on the number of bits allocated to the pixel. For example, when the number of bits of color allocated to the pixel is 8, the maximum value of the pixel may be 255. The color may be darker as the value of the pixel decreases, and the color may be brighter as the value of the pixel increases. Further, when the value of the pixel exceeds the first threshold value and is less than the second threshold value, the medical imaging apparatus 100 may determine the value of the pixel to be a median. The value of the pixel included in the black-and-white image may have only 0 (minimum value), the median, and the maximum value. The median may be an average value of 0 and the maximum value. The first threshold value and the second threshold value may be predetermined values. However, the present disclosure is not limited thereto, and the medical imaging apparatus 100 may determine the first threshold value and the second threshold value on the basis of the value of the pixel of the medical image.

The medical imaging apparatus 100 may extract only pixels of which values are greater than or equal to a predetermined third threshold value from the medical image. The medical imaging apparatus 100 may obtain a first quartile, a second quartile, and a third quartile of the maximum and minimum values of the extracted pixels. The medical imaging apparatus 100 may determine at least one of the first quartile, the second quartile, or an average value of the first and second quartiles as the first threshold value. Further, the medical imaging apparatus 100 may determine that at least one of the second quartile, the third quartile, or an average value of the second and third quartiles is the second threshold value.

The medical imaging apparatus 100 may perform an operation of determining whether a pre-stored pattern image appears in the black-and-white image. The pre-stored pattern image may be an image corresponding to the photographing position of the medical image. The pre-stored pattern image may include at least one of a pattern including only the maximum value of the pixel and a pattern including only the minimum value of the pixel. The pre-stored pattern image may have a size smaller than that of the black-and-white image. The pre-stored pattern image may include a pattern typically appearing in a medical image corresponding to a part to be photographed. There may be a plurality of pattern images corresponding to one part to be photographed. The medical imaging apparatus may determine whether at least one of the plurality of pattern images appears in the medical image. The medical imaging apparatus 100 may determine whether the pattern image is included in the black-and-white image by moving the pre-stored pattern image up, down, left, and right in the black-and-white image. The medical imaging apparatus 100 may compare the black-and-white image and the pattern image by replacing the pixel having the median in the black-and-white image with either the minimum value 0 or the maximum value.

When the pre-stored pattern image appears in the black-and-white image, the medical imaging apparatus 100 may perform an operation of replacing the template image corresponding to the photographing position of the medical image with the medical image. When the pre-stored pattern image does not appear in the black-and-white image, the medical imaging apparatus 100 may output a message indicating that the medical image is to be recaptured. There may be a plurality of pattern images corresponding to one part to be photographed. When at least one of the plurality of pattern images appears in the medical image, the medical imaging apparatus 100 may replace the template image corresponding to the photographing position of the medical image with the medical image.

The medical imaging apparatus 100 may determine the similarity between the medical image and the pattern image. Algorithms for determining similarity have already been listed above. When the similarity is greater than or equal to a predetermined threshold similarity, the medical imaging apparatus 100 may perform an operation of replacing the template image corresponding to the photographing position of the medical image with the medical image. When the similarity is less than the predetermined threshold similarity, the medical imaging apparatus 100 may output a message indicating that the medical image is to be recaptured.

As described above, the medical imaging apparatus 100 derives whether the medical image is properly captured by a simple comparison. The accuracy of confirming whether the medical image is properly captured may be somewhat low, but it is possible to rapidly determine whether the medical image is properly captured, and thus the medical imaging apparatus 100 may rapidly obtain a plurality of normal medical images. Further when the fact that a critically incorrect medical image was captured is found after all photographing is completed so that re-photographing is performed, fatigue of the user and the object may be increased, and the medical imaging apparatus 100 of the present disclosure may prevent such a problem from occurring.

After all the medical images for the plurality of photographing positions are obtained, the following process may be further performed. Alternatively, after the medical image for one photographing position among the plurality of photographing positions is obtained, the following process may be further performed. In the medical imaging apparatus 100, a predetermined measurement photographing position may be stored. The measurement photographing position may be a photographing position at which feature information of the object can be obtained. The medical imaging apparatus 100 may obtain the feature information of the object from the medical image corresponding to the measurement photographing position. The feature information of the object may include at least one of a development degree of the object, a degree of deformation of a body, a degree of deformity, a degree of health, and the like. In the medical image that does not correspond to the measurement photographing position, the feature information of the object may not be obtained or inaccurate feature information may be obtained. There may be a plurality of measurement photographing positions. The number of measurement photographing positions may be 4 or more and 20 or less. However, the present disclosure is not limited thereto.

For example, the feature information that can be obtained at a DP view, which is a measurement photographing position, may have a joint angle and a lateromedial deviation. The feature information that can be obtained at a lateral view, which is a measurement photographing position, may have a hoof wall angle and a P3 angle. Further, the feature information that can be obtained at a fetlock view, which is a measurement photographing position, may have a hoof-pastern axis (HPA).

When the medical image corresponding to the predetermined measurement photographing position is captured, the medical imaging apparatus 100 may perform an operation of obtaining the feature information from the medical image. More specifically, the medical imaging apparatus 100 may display at least one point for obtaining the feature information automatically or on the basis of the user's input, on the medical image. The medical imaging apparatus 100 may display at least one point for obtaining the feature information on the medical image using a machine learning model. The machine learning model may be a model obtained by machine-learning the coordinates of the at least one point on the medical image. The machine learning model may be pre-trained by the server. More specifically, in the server, the past medical image, and the coordinates of the at least one point of the past medical image may be stored. Coordinate values of an x-axis may increase toward a right side from an upper-left side of the medical image as the origin, and coordinate values of a y-axis may increase as it goes down. However, the present disclosure is not limited thereto. Coordinates of at least one point may be written by the user. The server may generate a machine learning model using a CNN. The server may machine-learn a correlation between the past medical image and the coordinates of at least one point. There may be only one machine learning model generated by the server. The medical imaging apparatus 100 may output the coordinates of the at least one point corresponding to the medical image by applying the medical image to the machine learning model. Alternatively, the medical imaging apparatus 100 may display the at least one point on the medical image. Further, the medical imaging apparatus 100 may obtain the feature information on the basis of the at least one point. The feature information may be obtained by a length of a line connecting one or more points, an angle between two lines, an angle formed by the line with the ground, and the like.

The present disclosure relates to a medical imaging apparatus, which can provide a guide for capturing a medical image of an equine so that a user can rapidly obtain the medical image of the equine. Further, the medical imaging apparatus of the present disclosure can provide accurate guide information so that even an unskilled person can rapidly adapt to photographing of the medical imaging apparatus.

Further, when the user obtains an image that can be captured first for each on-site situation, the medical imaging apparatus of the present disclosure can provide a photographing path that can reduce an image photographing time on the basis of the image captured first. Therefore, the user can rapidly obtain a plurality of medical images of the equine.

The effects obtainable in the present disclosure are not limited to the above-described effects and other effects that are not described may be clearly understood by those skilled in the art from the above detailed description.

While the present disclosure has been particularly described with reference to various embodiments, it will be understood by those skilled in the art that various changes in form and details may be made without departing from the spirit and scope of the present invention. Therefore, the disclosed embodiments should be considered from an exemplary point of view for description rather than a limiting point of view. The scope of the present invention is indicated in the claims rather than the foregoing description, and all differences within the scope equivalent thereto should be construed as being included in the present invention.

Meanwhile, the above-described embodiments of the present invention can be written as a program that can be executed on a computer, and can be implemented in a general purpose digital computer that operates a program using computer-readable recording media. The computer-readable recording media can include storage media such as magnetic storage media (e.g., a ROM, a floppy disk, a hard disk, etc.) and optically readable media (e.g., a compact disc read only memory (CD-ROM), a digital video disc (DVD), etc.).

What is claimed is:

1. An operating method of a medical imaging apparatus for capturing an X-ray medical image, the operating method comprising:
   receiving identification information of a user;
   receiving photographing mode selection information;
   determining that a photographing mode is an X-ray photographing mode for checking a health condition of an object on the basis of at least one of the identification information of the user and the photographing mode selection information;
   obtaining identification information of the object;
   determining an initial photographing position from among a plurality of predetermined photographing positions;
   determining a photographing sequence of the plurality of predetermined photographing positions on the basis of the initial photographing position;
   displaying a plurality of template images for the plurality of predetermined photographing positions according to the photographing sequence;
   highlighting a template image corresponding to a current photographing position on the basis of the photographing sequence;
   obtaining a medical image on the basis of the user's input;
   replacing the template image corresponding to the photographing position of the medical image with the medical image; and highlighting a template image corresponding to a next photographing position after the current photographing position on the basis of the photographing sequence.

2. The operating method of claim 1, wherein one template image among the plurality of template images includes information on a part of the object, information on a position of a detector with respect to the part of the object, and information on a position of a source.

3. The operating method of claim 1, wherein the replacing of the template image with the medical image includes:
converting the medical image into a black-and-white image;
determining whether a pre-stored pattern image appears in the black-and-white image; and
when it is determined that the pre-stored pattern image appears in the black-and-white image, replacing the template image corresponding to the photographing position of the medical image with the medical image,
wherein the pre-stored pattern image corresponds to the photographing position of the medical image.

4. The operating method of claim 1, further comprising:
obtaining diagnostic information on the medical image from the user;
obtaining a problem area and problem content which are included in the diagnostic information;
obtaining a deduction score on the basis of the problem area and the problem content; and
outputting the deduction score.

5. The operating method of claim 4, wherein the obtaining of the deduction score includes, when identical diagnostic information is obtained from different medical images obtained by photographing one part of the object at different angles, obtaining the deduction score using only the diagnostic information on one of the different medical images.

6. The operating method of claim 1, wherein the determining of the photographing sequence includes:
obtaining information on a state of the object in previous photographing on the basis of the identification information of the object;
when information on whether an accident occurs, which is included in the information on the state of the object in the previous photographing, indicates that no accident has occurred, obtaining a photographing sequence of the previous photographing, which is included in the information on the state of the object in the previous photographing; and
determining that the photographing sequence of the previous photographing is the photographing sequence,
wherein the information on the state of the object includes at least one of whether a stabilizer is administered, whether food is ingested before photographing, a photographing sequence, and whether an accident occurs.

7. The operating method of claim 1, wherein the determining of the initial photographing position includes:
displaying the plurality of template images for the plurality of predetermined photographing positions;
obtaining a medical image on the basis of the user's input;
determining a similarity between the medical image and each of the plurality of template images; and
determining that a photographing position corresponding to a template image having a highest similarity among the plurality of template images is the initial photographing position.

* * * * *